United States Patent [19]

Nagarajan

[11] 4,130,709
[45] Dec. 19, 1978

[54] PLEUROMUTILIN GLYCOSIDE DERIVATIVES

[75] Inventor: Ramakrishnan Nagarajan, Indianapolis, Ind.

[73] Assignee: Eli Lilly and Company, Indianapolis, Ind.

[21] Appl. No.: 858,507

[22] Filed: Dec. 8, 1977

[51] Int. Cl.$^2$ .............................................. C07G 11/00
[52] U.S. Cl. ...................................... 536/17; 424/180
[58] Field of Search .......................................... 536/17

[56] References Cited
PUBLICATIONS

Egger et al., Journ. of Antibiotics, vol. XXIX, No. 9, pp. 915–922.

Primary Examiner—Ethel G. Love
Attorney, Agent, or Firm—Nancy J. Harrison; Arthur R. Whale

[57] ABSTRACT

Pleuromutilin glycoside derivatives which are useful agents against gram-positive and gram-negative bacteria, anaerobic bacteria, and mycoplasma.

39 Claims, No Drawings

PLEUROMUTILIN GLYCOSIDE DERIVATIVES

BACKGROUND OF THE INVENTION

The antibiotic pleuromutilin was isolated in 1951 by Kavanagh et al. [Proc. Natl. Acad. Soc. 37, 570–574 (1951)]. The structure of pleuromutilin was later shown to be

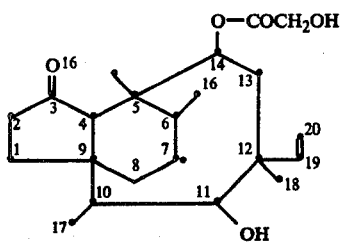

Alkaline hydrolysis of pleuromutilin gives a compound which is known as mutilin. Mutilin has the following structure:

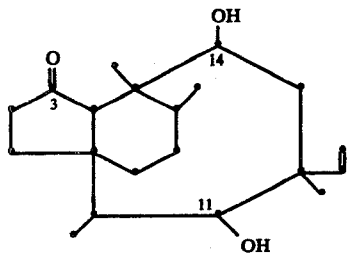

A great number of pleuromutilin derivatives have been prepared [Swiss Patent 572,894 (Derwent No. 26553X); Netherlands Patent 69,11083 (Derwent 40,642); Knauseder et al., U.S. Pat. No. 3,716,579; Egger et al., U.S. Pat. No. 3,919,290; Brandl et al., U.S. Pat. No. 3,949,079; Reidl, U.S. Pat. No. 3,979,423; Baughn et al., U.S. Pat. No. 3,987,194; Egger et al., U.S. Pat. No. 4,032,530; K. Reidl, "Studies on Pleuromutilin and Some of Its Derivatives," *J. Antibiotics* 29, 132–139 (1976); H. Egger and H. Reinshagen, "New Pleuromutilin Derivatives with Enhanced Antimicrobial Activity. I. Synthesis," *J. Antibiotics* 29, 915–922 (1976) and "II. Structure-Activity Correlations," ibid., 923–927 (1976); F. Knauseder and E. Brandl, "Pleuromutilins: Fermentation, Structure and Biosynthesis," *J. Antibiotics* 29, 125–131 (1976); J. Drews et al., "Antimicrobial Activities of 81.723 hfu, a New Pleuromutilin Derivative," *Antimicrob. Agents and Chemotherapy* 7, 507–516 (1975).

Recently, Michel and Higgens discovered antibiotic A-40104 factor A, which is a new member of the pleuromutilin family of antibiotics. This antibiotic is discussed in a co-pending patent application Ser No. 858,505, filed by Michel and Higgens, titled A-40104 ANTIBIOTICS AND PROCESS FOR PRODUCTION THEREOF, filed herewith this even date. The structure of antibiotic A-40104 factor A was found to be

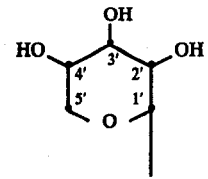

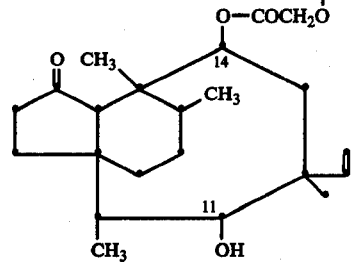

wherein the D-xylopyranose group is in the 62-configuration.

SUMMARY OF THE INVENTION

The present invention is directed to novel pleuromutilin glycoside derivatives having the following formula:

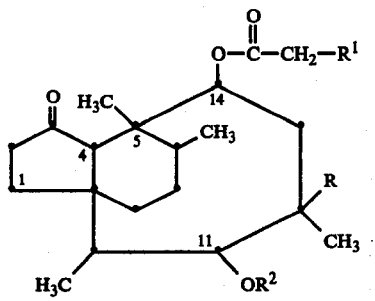

wherein R is ethyl or vinyl; $R^1$ is selected from the group consisting of:

(a) the $\alpha$- and $\beta$- anomers of the following hexopyranoses and hexofuranoses: D- and L-glucose; D- and L-galactose; D- and L-mannose; D- and L-gulose; D- and L-idose; D- and L-altrose; L- and D-rhamnose; D- and L-fucose; 1-thio-D- and L-glucose; 1-thio-D- and L-galactose; 1-thio-D- and L-mannose; 1-thio-D- and L-gulose; 1-thio-D- and L-idose; 1-thio-D- and L-altrose; 1-thio-L- and D-rhamnose; and 1-thio-D- and L-fucose;

(b) the $\alpha$- and $\beta$-anomers of the following pentopyranoses and pentofuranoses: D- and L-lyxose, D- and L-ribose, L- and D-arabinose, D- and L-2-deoxyribose; 1-thio-D- and L-lyxose, 1-thio-D- and L-ribose, 1-thio-L- and D-arabinose; and D- and L-2-deoxy-1-thioribose;

(c) the $\alpha$- and $\beta$-anomers of the following pentofuranoses: D- and L-xylose and 1-thio-D- and L-xylose;

(d) the $\alpha$- and $\beta$-anomers of the pentopyranose forms of L-xylose and 1-thio-D- and L-xylose;

(e) the $\alpha$-anomer of the pentopyranose form of D-xylose;

(f) the $\alpha$- and $\beta$-anomers of the following pyranose and furanose aminosugars: 2-deoxy-2-amino-D- and L-glucose; 2-deoxy-2-amino-D- and L-mannose; 2-deoxy-2-amino-D- and L-xylose; 2-deoxy-2-amino-D- and L-lyxose, 2-deoxy-2-amino-D- and L-galactose; 4-deoxy-4-amino-D- and L-xylose; 2-deoxy-2-amino-1-thio-D- and L-glucose; 2-deoxy-2-amino-1-thio-D- and L-mannose; 2-deoxy-2-amino-1-thio-D- and L-xylose; 2-deoxy-2-amino-1-thio-D- and L-lyxose; 1-thio-D- and L-galactosamine; 4-deoxy-4-amino-1-thio-D- and L-xylose; and the N-mono($C_1$-$C_4$)alkyl and N,N-di($C_1$-$C_4$)alkyl derivatives of these aminosugars;

(g) the α- and β-anomers of the following disaccharides: maltose; cellobiose; lactose; gentibiose; isomaltose; melibiose; raffinose; and xylobiose; 1-thiomaltose; 1-thiocellobiose; 1-thiolactose; 1-thiogentiobiose; 1-thioisomaltose; 1-thiomelibiose; 1-thioraffinose; and 1-thioxylobiose;

(h) the α- and β-anomers of the trisaccharides maltotriose; cellotriose; xylotriose; 1-thiomaltotriose; 1-thiocellotriose and 1-thioxylotriose;

(i) 2-deoxy-2-(hydroxyimino)-3,4,6-tri-O-acetyl-α-D-glucopyranosyl; 2-deoxy-2-(hydroxyimino)-3,4,6-tri-O-acetyl-α-D-galactopyranosyl; 2-deoxy-2-(hydroxyimino)-α-D-galactopyranosyl; 2-deoxy-2-amino-4,6-di-O-acetyl-α-D-glucopyranosyl; 2-deoxy-2acetamido-3,4,6-tri-O-acetyl-α-D-glucopyranosyl;

(j) and any of the (a) through (h) moieties peracylated with $C_2$-$C_4$-alkanoyl or benzoyl;

$R^2$ is hydrogen or, when $R^1$ is selected from the group defined in (j), $C_2$-$C_6$-alkanoyl or benzoyl; and the pharmaceutically-acceptable acid-addition salts of the compounds wherein $R^1$ is selected from the group defined in (f).

The compounds of this invention wherein $R^2$ is hydrogen are prepared by reacting pleuromutilin with the appropriate sugar moiety, using conventional methods for the formation of glycosides. For example, those glycosides which are β-anomers are, in general, prepared by the Koenigs-Knorr method (see, H. Krauch and W. Kunz, "Organic Name Reactions," John Wiley and Sons, New York, N.Y., 1964, page 269). The glycosides which are α-anomers are generally prepared by halo-catalyzed glycosidation. Bromo derivatives are especially preferred for these reactions.

Still another glycosidation method useful in the preparation of some of the compounds of the present invention involves the use of a mercuric compound such as, for example, mercuric cyanide as a catalyst.

It will be recognized that in these methods a per-O-acylglycosyl halide will be the appropriate starting sugar moiety. Preparation of these per-O-acylglycosyl halides is known in the art. For a review of the chemistry of these compounds, see Advan. Carbohyd. Chem. 10, 207-256 (1955). The per-O-acetylglycosyl halides are the most frequently used starting sugar moieties. Other acylglycosyl halides, however, such as per-O-($C_2$-$C_4$-alkanoyl)glycosyl halides and per-O-benzoylglycosyl halides are also useful. The bromides and chlorides are the most commonly used halide derivatives, since iodides decompose easily and fluorides are less reactive.

Another method of preparating some of the compounds of this invention involves reacting pleuromutilin with the nitrosyl chloride adduct of the per-O-acylated glycal derivative of the appropriate sugar to give the corresponding 2-(hydroxyimino) derivative, and subsequently converting this to the desired aminoglycoside.

The thioglycosides derivatives of the present invention wherein $R^2$ is hydrogen are prepared by reacting 14-deoxy-14-(monoiodoacetoxy)mutilin, hereinafter called iodopleuromutilin, with the appropriate per-O-acylmercapto sugar derivative. Iodopleuromutilin is prepared as described in U.S. Pat. No. 3,979,423. The per-O-acylated mercapto sugar derivatives can be prepared from the appropriate halo-substituted per-O-acylated sugar analogs by standard procedures. Another method of preparing the appropriate mercapto sugar derivatives involves boron trifluoride etherate catalysed condensation of the appropriate per-O-acyl sugar moiety with pleuromutilin thiol using the procedure described by R. J. Ferrier and R. H. Furneaux, *Carbohydrate Research* 52, 63–68 (1976).

2-Amino-1-thio-α-D-glycosides are conveniently prepared by condensation of 14-deoxy-14-(mercaptoacetoxy)-mutilin, hereinafter called pleuromutilin thiol, with the appropriate 2-deoxy-2-(hydroxyimino)-per-O-acyl-α-D-glycosyl chloride to give the corresponding 2-(hydroxyimino) derivative, followed by reduction of this oximino derivative to give the desired 2-amino compound.

Dialkylamino-1-thio-β-D-glycopyranosyl derivatives are prepared by converting dialkylamino-per-O-acyl-1-bromo-α-D-glycopyranosides [for preparation see J. Amer. Chem Soc. 99, 5826 (1977)] to the corresponding dialkylamino-per-O-acyl-1-mercapto-β-D-glycopyranosides and then coupling with iodopleuromutilin.

The compounds of the present invention wherein R is ethyl can be prepared from the corresponding compounds wherein R is vinyl by standard reduction procedures such as, for example, by hydrogenation with the use of palladium on carbon as a catalyst. These compounds can also be prepared by reacting 19,20-dihydropleuromutilin with the appropriate sugar moiety as above described.

Those compounds wherein $R^1$ is a per-O-acylated sugar moiety are useful 1) as intermediates to those compounds wherein $R^1$ is selected from the groups (a)–(h) and 2) as active compounds.

Those compounds wherein $R^1$ is selected from (a)–(h) are prepared from the appropriate per-O-acylated compounds wherein $R^1$ is (j) by cleaving the acyl groups in the presence of a base such as triethylamine.

The compounds wherein $R^2$ is $C_2$-$C_6$-alkanoyl or benzoyl are most conveniently prepared by first acylating iodopleuromutilin, using standard procedures, and then reacting the 11-deoxy-11-acyloxyiodopleuromutilin thus prepared with the appropriate per-O-acylmercapto sugar derivative, using conventional methods.

Preparation of the compounds of the present invention is further illustrated by the following specific examples:

EXAMPLE 1

Preparation of 14-deoxy-14-[(2,3,4,6-tetra-O-benzyl-α-D-glucopyranosyl)oxyacetoxy]mutilin 2,3,4,6-Tetra-O-benzyl-α-D-glucose (4.8012 g) and thionyl chloride (15 ml) were reacted with stirring in a 70° C. oil bath for 4 hours. The reaction mixture was evaporated under vacuum to give a thick oil. The oil was treated 3 times with toluene (about 30 ml), evaporating each time to remove excess $SOCl_2$, to give a yellow-brown oil (5.1931 g).

This oil was dissolved immediately in $CH_2Cl_2$ (35 ml). To the resulting solution was added ($C_2H_5$)$_4$NBr (1.6834 g); N,N-diisopropylethyl amine (2 ml) and pleuromutilin (1.743 g). The resulting mixture was stirred as room temperature in a tightly stoppered flask for one week. The reaction mixture was then diluted with an equal volume of $CH_2Cl_2$; this solution was washed sequentially with water, 1 N HCl and water. The $CH_2Cl_2$ layer was dried over $Na_2SO_4$, filtered, and evaporated to dryness under vacuum to give 5.5174 g of crude product.

This product was chromatographed over a 3.5- × 100-cm silica-gel (Merck) column, eluting with ethyl acetate; toluene (1:1) and collecting fractions having a volume of 8 ml at half hour intervals. Fractions were monitored by thin-layer chromatography (TLC) using the same adsorbent and solvent system and developing in an iodine chamber. Appropriate fractions were pooled and evaporated under vacuum to give 0.4624 g of 14-deoxy-14-[(2,3,4,6-tetra-O-benzyl-α-D-glucopyranosyl) oxyacetoxy]mutilin, yield 11.167%.

EXAMPLE 2

Preparation of
14-deoxy-14-[(α-D-glucopyranosyl)oxyacetoxy]-19,20-dihydromutilin 14-Deoxy-14-[(2,3,4,6-tetra-O-benzyl-α-D-glucopyranosyl)oxyacetoxyl]mutilin (400 mg), prepared as described in Example 1, was dissolved in ethanol (95%, 25 ml). This solution was added to 5% palladium on carbon (263 mg), and the mixture was allowed to react under an atmosphere of hydrogen for 1.5 days. The resulting reaction mixture was filtered through a sintered-glass funnel with a 3-cm layer of tightly packed celite. The filtrate was evaporated under vacuum to give 234.9 mg of 14-deoxy-14-[(α-D-glucopyranosyl)-oxyacetoxy]-19,20-dihydromutilin.

EXAMPLE 3

Preparation of
14-deoxy-14-[(2,3,4,6-tetra-O-acetyl-β-D-glucopyranosyl)oxyacetoxy]mutilin Pleuromutilin (1.6945 g, 4.48 mmoles) was dissolved in nitromethane:benzene (1:1, 300 ml); about 100 ml of this solution was distilled off to ensure dryness. $Hg(CN)_2$ (1.0694 g, 4.23 mmoles) was added to this solution. While the reaction mixture was maintained in a 60° oil bath under an atmosphere of nitrogen, a solution of acetobromoglucose (2.009 g, 4.89 mmoles) in nitromethane:benzene (1:1, 100 ml) was added dropwise over a 6-hour period. The reaction mixture was stirred for 20 hours under these conditions. At this point, more $Hg(CN)_2$ (762 mg, about 3 mmoles) was added to the reaction mixture, and a solution of 2,3,4,6-tetra-O-acetyl-α-D-glucopyranosyl bromide (964.2 mg, 2.34 mmoles) in nitromethane:benzene (1:1, 50 ml) was added dropwise as above. The reaction mixture was stirred for an additional 2 days. The reaction mixture was then cooled in an ice bath and washed sequentially with cold satureated $NaHCO_3$ solution (once) and cold saturated NaCl solution (twice). After each washing, the aqueous layer was back extracted with $CH_2Cl_2$. The organic layers were combined, dried over anhydrous $MgSO_4$ for 1 hour and then evaporated to dryness under vacuum to give 4.05 g of crude product.

This crude product was further purified by chromatography over a 3- × 95-cm silica-gel (Merck) column, eluting with ethyl acetate:toluene (1:1) and collecting fractions having a volume of about 8–10 ml at 45-minute intervals. The column fractions were monitored by silica-gel TLC, using an ethyl acetate:toluene (1:1) solvent system and iodine for detection. Appropriate fractions were pooled and evaporated under vacuum to give 515.3 mg of purified 14-deoxy-14-[(2,3,4,6-tetra-O-acetyl-β-D-glucopyranosyl)oxyacetoxy]-mutilin, a yield of 16.24%.

EXAMPLE 4

Preparation of
14-deoxy-14-[(β-D-glucopyranosyl)oxyacetoxy]-mutilin

14-Deoxy-14-[(2,3,4,6-tetra-O-acetyl-β-D-glucopyranosyl)oxyacetoxy]mutilin (1.237 g, about 1.74 mmoles), prepared as described in Example 3, was dissolved in anhydrous methanol (100 ml). To this solution were added water (100 ml) and then, with continued stirring at room temperature, distilled $(C_2H_5)_3N$ (30 ml). The resulting reaction mixture was stirred at room temperature for 3 days and then evaporated to dryness under vacuum. The residue still retained traces of $(C_2H_5)_3N$ and was further dried under vacuum to give 1.3762 g of crude product.

This crude product was further purified by chromatography over a 2-cm-diameter silica-gel column (150 g, Merck), eluting with ethhyl acetate:ethanol (4:1) and collecting fractions having a volume of about 2 ml at 20-minute intervals. The column was monitored by silica-gel TLC using the same solvent system and iodine for detection. Fractions No. 98–130 were combined and evaporated to dryness under vacuum to give 278.6 mg of 14-deoxy-14-[(β-D-glucopyranosyl)-oxyacetoxy]-mutilin.

EXAMPLE 5

Preparation of
14-deoxy-14-[(2-deoxy-2-(hydroxyimino)-3,4,6-tri-O-acetyl-α-D-glucopyranosyl)oxyacetoxy]mutilin Pleuromutilin (3.9797 g, 0.01052 mole) was dissolved in dimethylformamide (75 ml). D-Glucal triacetate NOCl adduct (3.6756 g, 0.0109 mole) was added to this solution. The reaction mixture was stirred at room temperature for 4 days and then was evaporated to dryness under vacuum. The dried residue was dissolved in $CH_2Cl_2$, and this solution was washed 4 times with saturated NaCl solution. The $CH_2Cl_2$ solution was dried over $MgSO_4$ for 30 minutes and then was evaporated to dryness under vacuum to give 7.25 g of crude product.

This crude product was further purified by chromatography over a 3.5- × 100-cm silica-gel column, eluting with ethyl acetate:toluene (1:1) and collecting fractions having a volume of about 10 ml at 45-minute intervals. The chromatography was monitored by silica-gel TLC using the same solvent system. Appropriate fractions were pooled and evaporated under vacuum to give 1.9 g of the desired product. Rechromatography of pools containing another impurity, using the same conditions, gave an additional 1.2141 g of product, giving a total of 3.1141 g of 14-deoxy-14-[(2-deoxy-2-(hydroxyimino)-3,4,6-tri-O-acetyl-α-D-glucopyranosyl)oxyacetoxy]mutilin, a yield of 43.67%.

EXAMPLE 6

Preparation of
14-deoxy-14-[(2-deoxy-2-(hydroxyimino)-3,4,6-tri-O-acetyl-α-D-glucopyranosyl)oxyacetoxy]-19,20-dihydromutilin 14-Deoxy-14-[(2-deoxy-2-(hydroxyimino)-3,4,6-tri-O-acetyl-α-D-glucopyranosyl)oxyacetoxy]multilin (3.5 g), prepared as described in Example 5, was dissolved in anhydrous ethanol (50 ml) and added to $PtO_2$ (2.9495 g) which was prereduced in anhydrous ethanol (50 ml) for 30 minutes. The resulting solution was hydrogenated for 1.5 days at room temperature. The reaction mixture was filtered through a sintered-glass funnel with a layer of celite. The filtrate was evaporated to dryness under vacuum and then was placed under high vacuum for 1 hour to remove solvent traces, giving 3.33 g of crude product.

This crude product was purified by chromatography over a 3- × 105-cm silica-gel column, eluting with toluene:acetone (2:1) and collecting fractions having a volume of 8–10 ml at 30 minute intervals. The chromatographic fractions were monitored by silica-gel TLC, using the same solvent system. Appropriate fractions were combined and evaporated under vacuum to dryness to give 2.5914 g of 14-deoxy-14-[(2-deoxy-2-(hydroxyimino)-3,4,6-tri-O-acetyl-α-D-glucopyranosyl)oxyacetoxy]-19,20-dihydromutilin.

EXAMPLE 7

Preparation of
14-deoxy-14-[(2-deoxy-2-(hydroxyimino)-3,4,6-tri-O-acetyl-α-D-galactopyranosyl)oxyacetoxy]mutilin Pleuromutilin (7.6342 g, 20.19 mmoles) was reacted with D-galactal triacetate NOCl adduct (7.6723 g, 22.76 mmoles) using the conditions described in Example 5 and purifying by silica-gel chromatography, using an ethyl acetate:toluene (1:1) solvent system, to give 14-deoxy-14-[(2-deoxy-2-(hydroxyimino)-3,4,6-tri-O-acetyl-α-D-galactopyranosyl)oxyacetoxy]mutilin (10.0739 g, 14.8 mmoles) in a yield of 73%.

EXAMPLE 8

Preparation of
14-deoxy-14-[(2-deoxy-2-(hydroxyimino)-α-D-galactopyranosyl)oxyacetoxy]mutilin 14-Deoxy-14-[(2-deoxy-2-(hydroxyimino)-3,4,6-tri-O-acetyl-α-D-galactopyranosyl)oxyacetoxy]mutilin (1.5 g), prepared as described in Example 7, was dissolved in methanol (50 ml) and water (50 ml). $(C_2H_5)_3N$ (50 ml) was added to the solution. The resulting solution was stirred at room temperature for 3 days. The reaction mixture was then evaporated under vacuum. $CHCl_3$ was added, and the residue was placed under vacuum, causing it to foam; the residue was placed under high vacuum for 1 hour to give 414 mg of crude product.

The crude product was dissolved in a minimal amount of methanol and placed on a 1.5- × 70-cm silica-gel (Merck) column, eluting with ethyl acetate:ethanol (9:1) and collecting fractions having a volume of about 2–3 ml at 1 hour intervals. The fractions were monitored by silica-gel TLC using the same solvent system. Appropriate fractions were pooled and evaporated to dryness to give a total of 104.4 mg of 14-deoxy-14-[(2-deoxy-2-(hydroxyimino)-α-D-galactopyranosyl)oxyacetoxy]mutilin.

EXAMPLE 9

Preparation of
14-deoxy-14-[(2-deoxy-2-amino-4,6-di-O-acetyl-α-D-glucopyranosyl)oxyacetoxy]-19,20-dihydromutilin 14-Deoxy-14-[(2-deoxy-2-(hydroxyimino)-3,4,6-tri-O-acetyl-α-D-glucopyranosyl)oxyacetoxy]mutilin (508.6 mg), prepared as described in Example 5, was dissolved in absolute ethanol (50 ml) and hydrogenated with Raney nickel (0.5 g) at room temperature overnight. The resulting reaction mixture was filtered through a sintered-glass funnel with a layer of celite. The filtrate was evaporated to dryness, redissolving in a small amount of $CHCl_3$ and reevaporating under vacuum to dryness to give a white foam. The foam was placed under high vacuum for about 2 hours to give 381.7 mg of crude product.

This crude product was dissolved in a minimal amount of methanol and chromatographed over a 1.5- × 75-cm silica-gel (Merck) column. The column was eluted with acetonitrile:water (4:1), collecting fractions having a volume of about 2–3 ml at 60-minute intervals. The column was monitored by silica-gel TLC using both the column solvent system and also an ethyl acetate:ethanol (9:1) solvent system. Appropriate fractions were pooled and evaporated under vacuum to give 25.5 mg of 14-deoxy-14-[(2-deoxy-2-amino-4,6-di-O-acetyl-α-D-glucopyranosyl)oxyacetoxy]-19,20-dihydromutilin.

EXAMPLE 10

Preparation of
11-acetyl-14-deoxy-14-[(2-deoxy-2-acetamido-3,4,6-tri-O-acetyl-α-D-glucopyranosyl)oxyacetoxy]-19,20-dihydromutilin 14-Deoxy-14-[(2-deoxy-2-amino-4,6-di-O-acetyl-α-D-glucopyranosyl)oxyacetoxy]-19,20-dihydromutilin (17 mg) prepared as described in Example 9, was acetylated overnight under standard conditions with acetic anhydride (0.5 ml) and pyridine (0.5 ml). The reaction mixture was added to cold water; the aqueous solution was extracted with $CHCl_3$. The resulting $CHCl_3$ solution was washed with 1 N HCl and saturated $NaHCO_3$ solution, was dried over anhydrous $Na_2SO_4$ and evaporated to give 9 mg of 11-acetyl-14-deoxy-14-[(2-deoxy-2-acetamido-3,4,6-tri-O-acetyl-α-D-glucopyranosyl)oxyacetoxy]-19,20-dihydromutilin.

EXAMPLE 11

Preparation of
14-deoxy-14-[(2-deoxy-2-amino-α-D-galactopyranosyl)oxyacetoxy]-19,20-dihydromutilin 14-Deoxy-14-[(2-deoxy-2-(hydroxyimino)-α-D-galactopyranosyl)oxyacetoxy]mutilin (566.6 mg, 1.02459 mmoles), prepared as described in Example 8, was dissolved in ethanol (25 ml). To this solution were added 5% palladium on carbon (333 mg) and 1 N HCl (1.2 ml). The resulting solution was hydrogenated at room temperature for about 4 days; after removal of the catalyst, the filtrate was evaporated under vacuum to dryness. The residue was placed under high vacuum for at least 4 hours to give 606.7 mg of crude product as a white foam. This crude product was further purified by chromatography over a 2.7-cm-diameter silica-gel column (150 g, Merck) using $CH_3CN:H_2O$ (9:1) and collecting fractions having a volume of about 4 ml at 30-minute intervals. The column was monitored by silica-gel TLC using the same solvent system and iodine for detection. Fractions were evaporated to dryness under vacuum. Fractions No. 371–420 were combined to give 33.2 mg of 14-deoxy-14-[(2-deoxy-2-amino-α-D-galactopyranosyl)oxyacetoxy]-19,20-dihydromutilin.

EXAMPLE 12

Preparation of 14-deoxy-14-[(2,3,4,6-tetra-O-acetyl-β-D-glucopyranosyl)thioacetoxy]mutilin A solution of iodopleuromutilin (577.3 mg), prepared as described in Example 3 of U.S. Pat. No. 3,979,423, in acetone (2 ml) was added to a solution of 2,3,4,6-tetra-O-acetyl-β-D-glucopyranosyl mercaptan (428.8 mg) in acetone (2 ml). A solution of $K_2CO_3$ (168.4 mg) in water (1 ml) was added to the stirring reaction mixture; the resulting solution was stirred at room temperature for 30 minutes. The reaction mixture was then poured into deionized water (25 ml); the aqueous solution was extracted with $CH_2Cl_2$. The $CH_2Cl_2$ solution was dried over $Na_2SO_4$, filtered and evaporated to dryness under vacuum. The residue was dried under high vacuum for 1.5 hours to give 989.7 mg of 14-deoxy-14-[(2,3,4,6-tetra-O-acetyl-β-D-glucopyranosyl)thioacetoxy]mutilin.

EXAMPLE 13

Preparation of 14-deoxy-14-[(2,3,4,6-tetra-O-acetyl-β-D-glucopyranosyl)thioacetoxy]-19,20-dihydromutilin 14-Deoxy-14-[(2,3,4,6-tetra-O-acetyl-β-D-glucopyranosyl)thioacetoxy]mutilin (611 mg), prepared as described in Example 12, was dissolved in ethanol (55 ml); 5% palladium on carbon (495 mg) was added. The reaction mixture was hydrogenated for about 10 hours and then was filtered through a sintered-glass filter over celite. The filtrate was evaporated to dryness under vacuum, reevaporating from a small amount of $CHCl_3$ to give 500 mg of 14-deoxy-14-[(2,3,4,6-tetra-O-acetyl-β-D-glucopyranosyl)thioacetoxy]-19,20-dihydromutilin as a white foam.

EXAMPLE 14

Preparation of 14-deoxy-14-[(β-D-glucopyranosyl)thioacetoxy]-mutilin

14-Deoxy-14-[(2,3,4,6-tetra-O-acetyl-β-D-glucopyranosyl)thioacetoxy]mutilin (529.8 mg), prepared as described in Example 13, was dissolved in methanol (50 ml). Water (50 ml) and $(C_2H_5)_3N$ (50 ml) were added to this solution. The resulting solution was stirred at room temperature for 3 days and then evaporated to dryness under vacuum to remove all traces of solvent. The residue was reevaporated from $CHCl_3$ to give 492 mg of crude product.

This product was further purified by chromatography over a 2-cm-diameter silica-gel column (150 g, Merck), eluting with ethyl acetate:ethanol (9:1) and collecting fractions having a volume of about 6 ml at 30-minute intervals. The fractions were monitored by silica-gel TLC using the same solvent system and iodine for detection. Fractions No. 28–120 were combined and evaporated to give 366 mg of 14-deoxy-14-[(β-D-glucopyranosyl)thioacetoxy]mutilin.

EXAMPLE 15

Preparation of 14-deoxy-14-[(β-D-glucopyranosyl)thioacetoxy]-19,20-dihydromutilin 14-Deoxy-14-[(β-D-glucopyranosyl)thioacetoxy]-mutilin (465.5 mg), prepared as described in Example 14, was dissolved in warm tetrahydrofuran (100 ml). To this solution was added 5% palladium on carbon (250 mg); the mixture was hydrogenated at room temperature for 7 hours. The resulting reaction mixture was filtered through a sintered-glass funnel with a layer of celite. The filtrate was evaporated to dryness under high vacuum to give 500 mg of 14-deoxy-14-[(β-D-glucopyranosyl)thioacetoxy]-19,20-dihydromutilin.

EXAMPLE 16

A. Preparation of 2,3,4-tri-O-acetyl-1-thiouronium-β-D-xylopyranose hydrobromide 2,3,4-Tri-O-acetyl-α-D-xylopyranosyl bromide (1.3 g, 3.83 mmoles), prepared as described in "Methods of Carbohydrate Chemistry," Vol. 1, Academic Press, New York, N.Y., 1962, p. 183, was dissolved in acetone (3 ml). Thiourea (330 mg, 4.33 mmoles) was added to this solution. After adding additional acetone (about 3 ml), the resulting solution was heated under reflux (oil bath at 70° C.) for about 20 minutes. The product crystallized upon cooling the reaction mixture in an ice bath. The crystals were separated by filtration, washed with a minimal amount of acetone, and dried to give 849 mg of 2,3,4-tri-O-acetyl-1-thioronium-β-D-xylopyranose hydrobromide, m.p. 174°–175° C.

B. Preparation of 2,3,4-tri-O-acetyl-1-thio-β-D-xylopyranose

Water (5 ml) and $CCl_4$ (5 ml) were added to 2,3,4-tri-O-acetyl-1-thioronium-β-D-xylopyranose hydrobromide (608.4 mg, 1.466 mmoles), prepared as described in Sect. A, and $Na_2S_2O_5$ (218 mg, 1.14 mmoles). The reaction mixture was heated under reflux for 40 minutes and then cooled to room temperature. The $CCl_4$ layer was separated. THe aqueous layer was washed twice with 10-ml portions of $CCl_4$. The $CCl_4$ fractions were combined, dried over anhydrous $Na_2SO_4$, filtered, and evaporated under vacuum to give 212.9 mg of 2,3,4-tri-O-acetyl-1-thio-β-D-xylopyranose as a yellow oil. This preparation required further purification over a silica-gel column to give an oil (132.3 mg) which crystallized (m.p. 117°–122° C.). In later preparations this final chromatographic purification was not required; the product crystallized directly upon seeding.

C. Preparation of 14-deoxy-14-[(2,3,4-tri-O-acetyl-β-D-xylopyranosyl)-thioacetoxy]mutilin 2,3,4-Tri-O-acetyl-1-thio-β-D-xylopyranose (1.46 g, 5 mmoles), prepared as described in Sect. B, was dissolved in acetone (10 ml). A solution of iodopleuromutilin (2.48 g, 5.08 mmoles) in acetone (10 ml) was added. To the stirring reaction mixture was added a solution of $K_2CO_3$ (721 mg, 5.19 mmoles) in water (5 ml). The resulting solution was stirred at room temperature for 20 minutes and then poured into deionized water (100 ml). This solution was extracted with $CH_2Cl_2$. The $CH_2Cl_2$ solution was dried over anhydrous $Na_2SO_4$, filtered, evaporated to dryness under vacuum, and further dried under high vacuum for 8 hours to give 3.8246 g of product as a white foam which crystallized either from diethyl ether-hexane or from diethyl ether-ethyl acetate, m.p. 91°–97° C.

EXAMPLE 17

Preparation of 14-deoxy-14-[(2,3,4-tri-O-acetyl-β-D-xylopyranosyl)-thioacetoxy]-19,20-dihydromutilin 14-Deoxy-14-[(2,3,4-tri-O-acetyl-β-D-xylopyranosyl)thioacetoxy]mutilin (523 mg), prepared as described in Example 16, was dissolved in ethanol (20 ml). To this solution was added 5% palladium on carbon (216 mg). The resulting mixture was hydrogenated at room temperature for 11.5 hours. The reaction mixture was filtered through a layer of celite. The filtrate was evaporated under vacuum to give 14-deoxy-14-[(2,3,4-tri-O-acetyl-β-D-xylopyranosyl)thioacetoxy]-19,20-dihydromutilin (446 mg).

EXAMPLE 18

Preparation of 14-deoxy-14-[(β-D-xylopyranosyl)thioacetoxy]-mutilin

14-Deoxy-14-[(2,3,4-tri-O-acetyl-β-D-xylopyranosyl)thioacetoxy]mutilin (1.5954 g), prepared as described in Example 16, was dissolved in methanol (60 ml); water (50 ml) and $(C_2H_5)_3N$ (55 ml) were added. The resulting reaction mixture was stirred at room temperature for 2 days and then was evaporated under vacuum to dryness. The residue was redissolved in $CHCl_3$ and reevaporated about 4 times. The residue was dried under high vacuum about 4 hours to yield 1.79 g of crude product.

This product was purified by chromatography over a 2.7-cm-diameter silica-gel column (200 g, Merck), eluting with ethyl acetate:ethanol (9:1) and collecting fractions having a volume of about 5 ml at 20-min intervals. The fractions were monitored by silica-gel TLC using the same solvent and iodine for detection. Fractions No. 38–60 were combined and evaporated under vacuum to give 1.2066 g of 14-deoxy-14-[(β-D-xylopyranosyl)thioacetoxy]mutilin.

EXAMPLE 19

Preparation of 14-deoxy-14-[(β-D-xylopyransoyl)thioacetoxy]-19,20-dihydromutilin 14-Deoxy-14-[(β-D-xylopyranosyl)thioacetoxy]mutilin (285 mg), prepared as described in Example 18, was dissolved in ethanol (10 ml); 5% palladium on carbon (145 mg) was added. The resulting mixture was hydrogenated at room temperature for 7 hours and then was filtered through celite. The filtrate was evaporated to give a white foam which was further dried under high vacuum for about 30 minutes to give a quantitative yield of product. Product similarly prepared (7.75 g) was crystallized from ethyl acetate (15 ml) to give 5.87 g of 14-deoxy-14-[(β-D-xylopyranosyl)thioacetoxy]-19,20-dihydromutilin, m.p. 93°–95° C.

EXAMPLE 20

Preparation of 14-Deoxy-14-[(2,3,4-tri-O-acetyl-β-D-arabinopyranosyl)thioacetoxy]mutilin 2,3,4-Tri-O-acetyl-1-thio-β-D-arabinose (3.177 g, 0.0109 moles), prepared using the procedures described in Example 16, Sections A and B, dissolved in acetone (20 ml) and iodopleuromutilin (5.31 g, 0.0109 moles), also dissolved in acetone (20 ml), were mixed together. $K_2CO_3$ (1.506 g, 0.0109 moles) in water (10 ml) was added. The resulting solution was stirred at room temperature for 30 minutes and then poured into water (100 ml). The aqueous solution was extracted three times with 50-ml portions of $CH_2Cl_2$. The $CH_2Cl_2$ extracts were combined, dried over anhydrous $Na_2SO_4$, and filtered; the filtrate was evaporated to dryness under vacuum to give 7.1 grams of crude product.

This product was further purified by high performance liquid chromatography (HPLC; Waters' Associates Prep. LC/System 500), eluting with a toluene:ethyl acetate (1:1) solvent system at a flow rate of 250 ml/min, collecting fractions having a volume of 250 ml. Fraction content was monitored by silica-gel TLC, using a toluene:ethyl acetate (1:1) solvent and iodine detection. Fractions 17–22 contained the maximum amount of purified product. These fractions were combined and evaporated under vacuum to give 4.989 g of 14-deoxy-14-[(2,3,4-tri-O-acetyl-β-D-arabinopyranosyl)thioacetoxy]mutilin.

EXAMPLE 21

Preparation of 14-Deoxy-14-[(2,3,4-tri-O-acetyl-β-D-arabinopyranosyl)thioacetoxy]-19,20-dihydromutilin 14-Deoxy-14-[(2,3,4-tri-O-acetyl-β-D-arabinopyranosyl)thioacetoxy]mutilin (100 mg), prepared as described in Example 20, was dissolved in anhydrous ethanol (10 ml); 5% palladium on carbon (25 mg) was added. The reaction mixture was hydrogenated overnight and then filtered through celite to remove the catalyst. The solvent was evaporated under vacuum to give 100.5 mg of 14-deoxy-14-[(2,3,4-tri-O-acetyl-β-D-arabinopyranosyl)thioacetoxy]-19,20-dihydromutilin.

EXAMPLE 22

Preparation of 14-Deoxy-14-[(β-D-arabinopyranosyl)thioacetoxyl]-mutilin

14-Deoxy-14-[(2,3,4-tri-O-acetyl-β-D-arabinopyranosyl)thioacetoxy]mutilin (1 g), prepared as described in Example 20, was dissolved in methanol (50 ml); water (50 ml) and then triethylamine (50 ml) were added to this solution. The resulting solution was stirred at room temperature for 48 hours. The solvent was then evaporated under vacuum to give a crude product. This product was further purified by HPLC as described in Example 20, eluting with a gradient solvent [from ethyl acetate to ethyl acetate: 95% ethanol (9:1)], to give 0.62 g of 14-deoxy-14-[(β-D-arabinopyranoxyl)thioacetoxy]-mutilin.

EXAMPLE 23

Preparation of 14-deoxy-14-[(β-D-arabinopyranosyl)thioacetoxy]-19,20-dihydromutilin 14-Deoxy-14-[(β-D-arabinopyranosyl)thioacetoxy]-mutilin (100 mg), prepared as described in Example 22, was hydrogenated for 24 hours, using the procedure described in Example 21, to give 100 mg of 14-deoxy-14-[(β-D-arabinopyranosyl)thioacetoxy]-19,20-dihydromutilin.

EXAMPLE 24

Preparation of
14-Deoxy-14-[(2,3,4-tri-O-acetyl-β-L-arabinopyranosyl)thioacetoxy]mutilin Iodopleuromutilin (4.636 g, 0.0095 moles) was reacted with 2,3,4-tri-O-acetyl-1-thio-L-arabinose (2.76 g, 0.0095 moles) according to the method described in Example 20 to give 6.265 g of crude product which was purified by HPLC as described in Example 20, using a gradient solvent from 4 l. of toluene to 4 l. of toluene:ethyl acetate (1:1), to give 3.53 g of 14-deoxy-14-[(2,3,4-tri-O-acetyl-β-L-arabinopyranosyl)thioacetoxy]mutilin.

EXAMPLE 25

Preparation of
14-Deoxy-14-[(β-L-arabinopyranosyl)thioacetoxy]mutilin

14-Deoxy-14-[(2,3,4-tri-O-acetyl-β-L-arabinopyranosyl)thioacetoxy]mutilin (1 g), prepared as described in Example 24, was deacylated according to the procedure described in Example 22 to give 1.09 g of crude product. This product was purified by HPLC, using a gradient solvent from 4 l. of ethyl acetate to 4 l. of ethyl acetate:ethanol (9:1), to give 0.6862 g of 14-deoxy-14-[(β-L-arabinopyranosyl)thioacetoxy]mutilin.

EXAMPLE 26

14-Deoxy-14-[(2,3,4-tri-O-acetyl-β-L-arabinopyranosyl)thioacetoxy]-19,20-dihydromutilin, prepared from 14-deoxy-14-[(2,3,4-tri-O-acetyl-β-L-arabinopyranosyl)thioacetoxy]mutilin according to the procedure described in Example 21.

EXAMPLE 27

14-Deoxy-14-[(β-L-arabinopyranosyl)thioacetoxy]-19,20-dihydromutilin, prepared from 14-deoxy-14-[β-L-arbinopyranosyl)thioacetoxy]mutilin according to the procedure described in Example 23.

EXAMPLE 28

Preparation of
14-Deoxy-14-[(2,3,4,6-tetra-O-acetyl-β-D-galactopyranosyl)thioacetoxy]mutilin Iodopleuromutilin (9.27 g, 0.019 moles) was reacted with 2,3,4,6-tetra-O-acetyl-β-D-galactopyranosyl mercaptan (6.96 g, 0.019 moles) according to the method described in Example 12 to give 14.14 g of crude product. This product was purified using HPLC, as described in Example 20, using a gradient solvent from 4 l. of toluene to 4 l. of a toluene:ethyl acetate (1:1) (8 liters) and monitoring with TLC to give 3.99 g of 14-deoxy-14-[(2,3,4,6-tetra-O-acetyl-β-D-galactopyranosyl)thioacetoxy]mutilin.

EXAMPLE 29

Preparation of
14-Deoxy-14-[β-D-galactopyranosyl)thioacetoxy]-19,20-dihydromutilin 14-Deoxy-14-[(2,3,4,6-tetra-O-acetyl-β-D-galactopyranosyl)thioacetoxy]mutilin (200 mg), prepared as described in Example 28, was hydrogenated for 20 hours, using the procedure described in Example 13, to give 0.19 g of 14-deoxy-14-[(2,3,4,6-tetra-O-acetyl-β-D-galactopyranosyl)thioacetoxy]-19,20-dihydromutilin.

EXAMPLE 30

Preparation of
14-Deoxy-14-[(β-D-galactopyranosyl)thioacetoxy]mutilin

14-Deoxy-14-[(2,3,4,6-tetra-O-acetyl-β-D-galactopyranosyl)thioacetoxy]mutilin (1 g), prepared as described in Example 28, was deacetylated using the method described in Example 14 to give 1.16 g of crude product. This product was further purified by HPLC as described in Example 20, but using a gradient solvent from 4 l. of ethyl acetate to 4 l. of ethyl acetate:ethanol (9:1) to give 0.49 g of 14-deoxy-14-[(β-D-galactopyranosyl)thioacetoxy]mutilin.

EXAMPLE 31

14-Deoxy-14-[(β-D-galactopyranosyl)thioacetoxy]-19,20-dihydromutilin, prepared from 14-deoxy-14-[(β-D-galactopyranosyl)thioacetoxy]mutilin as described in Example 15.

EXAMPLE 32

14-Deoxy-14-[(2,3,4-tri-O-acetyl-β-L-xylopyranosyl)thioacetoxy]mutilin was prepared using the procedure described in Example 16 but starting with L-xylose. In the final step iodopleuromutilin (31 g) was reacted with 2,3,4-tri-O-acetyl-1-thio-β-L-xylose (19 g) to give 39.6 g of crude product. This crude product was purified by HPLC, as described in Example 20, but using a gradient solvent system (8 l.) from toluene to toluene:ethyl acetate (7:3). The purified fractions crystallized from toluene:ethyl acetate to give 21.05 g of 14-deoxy-14-[(2,3,4-tri-O-acetyl-β-L-xylopyranosyl)thioacetoxy]mutilin, m.p. 210°–213° C.

EXAMPLE 33

14-Deoxy-14-[(2,3,4-tri-O-acetyl-β-L-xylopyranosyl)thioacetoxy]-19,20-dihydromutilin was prepared from 14-deoxy-14-[(2,3,4-tri-O-acetyl-β-L-xylopyranosyl)thioacetoxy]-mutilin (2.56 g; prepared as described in Example 32), using the procedure described in Example 19 to give 2.23 g of product.

EXAMPLE 34

14-Deoxy-14-[(β-L-xylopyranosyl)thioacetoxy]mutilin, prepared from 14-deoxy-14-[(2,3,4-tri-O-acetyl-β-L-xylopyranosyl)thioacetoxy]mutilin (15.8 g; prepared as described in Example 32) according to the procedure described in Example 18 to give 14.3 g of product as a white foam.

EXAMPLE 35

14-Deoxy-14-[(β-L-xylopyranosyl)thioacetoxy]-19,20-dihydromutilin, prepared from 14-deoxy-14-[(β-L-xylopyranosyl)thioacetoxy]mutilin (7 g; prepared as described in Example 34) according to the procedure described in Example 19 to give 6.3 g of product as a white foam.

EXAMPLE 36

A. Preparation of Pleuromutilin Thiouronium Hydroiodide

Iodopleuromutilin (46.8 g) was dissolved in acetone (300 ml); thiourea (7.418 g) and more acetone (60 ml) were added to this solution. The resulting reaction mixture was heated under reflux in a 90° C. oil bath for about 30 minutes. After the reaction mixture was allowed to cool to room temperature, it was evaporated to dryness under vacuum to give 60 g of 14-deoxy-14-(thiouronium acetoxy)mutilin hydroiodide, hereafter called pleuromutilin thiouronium hydroiodide, as a white amorphous compound.

B. Preparation of Pleuromutilin Thiol

Pleuromutilin thiouronium hydroiodide (60 g), prepared as described in Section A, was dissolved in water (200 ml) and sufficient warm methanol to give a complete solution. $Na_2S_2O_5$ (23 g), dissolved in water (100 ml), and $CCl_4$ (150–200 ml) were added to this solution. The resulting reaction mixture was heated under reflux in an 80°–90° C. oil bath for about 30 minutes. The chloroform layer was separated, dried over anhydrous $Na_2SO_4$, and evaporated to dryness to give 32.5 g of pleuromutilin thiol as a white amorphous compound.

C. Preparation of α- and β-anomers of 14-deoxy-14-[(2,3,4-tri-O-acetyl-D-ribopyranosyl)thioacetoxy]mutilin Pleuromutilin thiol (7.53 g, 19.1 mmoles), prepared as described in Section B, was dissolved in $CHCl_3$ (100 ml); tetra-O-acetylribopyranose (6.19 g, 19.46 mmoles) was added. To the resulting solution was added $BF_3$ etherate (9 ml). The resulting reaction mixture was stirred at room temperature for about 2½ hours and then was evaporated to dryness under vacuum. The residue thus obtained was redissolved in $CHCl_3$ and washed twice with an equal volume of water. The $CHCl_3$ layer was separated, dried over anhydrous $Na_2SO_4$ overnight and then was evaporated to dryness under vacuum to give 13 g of a mixture of the α- and β-anomers of 14-deoxy-14-[(2,3,4-tri-O-acetyl-D-ribopyranosyl)thioacetoxy]-mutilin. This crude product was further purified over HPLC as described in Example 20, using first a gradient solvent from 4 l. of toluene to 4 l. of toluene:ethyl acetate (3:1); then using 4 l. of toluene:ethyl acetate (3:1) and finally 2 l. of ethyl acetate. Appropriate fractions from this HPLC were further purified over another HPLC using first 4 l. of toluene and then a gradient solvent of 4 l. of toluene to 4 l. of toluene:ethyl acetate (4:1). Again, appropriate fractions were combined to give a purified product. This product (still a mixture of anomers) was further purified over a 3.5-cm-diameter silica-gel column, using a toluene:isobutyl alcohol (9:1) solvent system and collecting fractions having a volume of about 5 ml at 30-minute intervals. The fractions were also monitored by TLC. 307.3 mg of the α-anomer and 1.32 g of the β-anomer were isolated.

EXAMPLE 37

14-Deoxy-14-[(α-D-ribopyranosyl)thioacetoxy]mutilin, prepared from 14-deoxy-14-[(2,3,4-tri-O-acetyl-α-D-ribopyranosyl)thioacetoxy]mutilin (prepared as described in Example 36) according to the method described in Example 14.

EXAMPLE 38

14-Deoxy-14-[(β-D-ribopyranosyl)thioacetoxy]mutilin, prepared from 14-deoxy-14-[(2,3,4-tri-O-acetyl-β-D-ribopyranosyl)thioacetoxy]mutilin (prepared as described in Example 36) according to the procedure of Example 14.

EXAMPLE 39

14-Deoxy-14-[(α-D-ribopyranosyl)thioacetoxy]-19,20-dihydromutilin, prepared from 14-deoxy-14-[(α-D-ribopyranosyl)thioacetoxy]mutilin (prepared as described in Example 37) according to the method of Example 19.

EXAMPLE 40

14-Deoxy-14-[(β-D-ribopyranosyl)thioacetoxy]-19,20-dihydromutilin, prepared from 14-deoxy-14-[(β-D-ribopyranosyl)thioacetoxy]mutilin (prepared as described in Example 38) according to the procedure of Example 19.

EXAMPLE 41

Preparation of the α- and β-anomers of 14-deoxy-14-[(2,3,5-tri-O-acetyl-D-ribofuranosyl)thioacetoxy]mutilin Pleuromutilin thiol (6.5 g, 16.49 mmoles), prepared as described in Example 36 Section B, was dissolved in chloroform (150 ml); tetra-O-acetyl-β-D-ribofuranose (6.9 g, 21.69 mmoles) was added to this solution. To the resulting solution was gradually added $BF_3$ etherate (10 ml). The reaction was carried out according to the procedure described in Example 36 Section C to give 10 g of crude product which was a mixture of anomers.

This mixture was separated by HPLC, as described in Example 20, using first an 8-liter gradient solvent from toluene to toluene:ethyl acetate (3:1) and then another 8-liter gradient from toluene-ethyl acetate (3:1) to toluene:ethyl acetate (1:3) to give purified crude product (1.6589 g). This product was chromatographed over a 2.5-cm-diameter column of silica gel (225 g, Merck), using a toluene:isobutyl alcohol (9:1) solvent system and collecting fractions having a volume of 3 ml at 30-minute intervals. Fractions No. 205–250 were pooled and evaporated under vacuum to give 0.494 g of further purified material. This material was rechromatographed over another silica-gel column using the same conditions. Fractions No. 209–215 were pooled and evaporated under vacuum to give 56 mg of 14-deoxy-14-[(2,3,5-tri-O-acetyl-α-D-ribofuranosyl)thioacetoxy]mutilin. Fractions No. 248–260 were similarly combined to give 28 mg of 14-deoxy-14-[(2,3,5-tri-O-acetyl-β-D-ribofuranosyl)thioacetoxy]mutilin.

EXAMPLE 42

14-Deoxy-14-[(2,3,5-tri-O-acetyl-α-D-ribofuranosyl)thioacetoxy]-19,20-dihydromutilin, prepared from 14-deoxy-14-[(2,3,5-tri-O-acetyl-α-D-ribofuranosyl)thioacetoxy]mutilin (prepared as described in Example 41) according to the procedure of Example 17.

EXAMPLE 43

14-Deoxy-14-[(2,3,5-tri-O-acetyl-β-D-ribofuranosyl)thioacetoxy]-19,20-dihydromutilin, prepared from 14-deoxy-14-[(2,3,5-tri-O-acetyl-β-D-ribofuranosyl)thioacetoxy]mutilin (prepared as described in Example 41) according to the procedure of Example 17.

EXAMPLE 44

14-Deoxy-14-[(α-D-ribofuranosyl)thioacetoxy]-mutilin, prepared from 14-deoxy-14-[(2,3,5-tri-O-acetyl-α-D-ribofuranosyl)thioacetoxy]mutilin (prepared as described in Example 41) according to the procedure of Example 18.

EXAMPLE 45

14-Deoxy-14-[(β-D-ribofuranosyl)thioacetoxy]-mutilin, prepared from 14-deoxy-14-[(2,3,5-tri-O-acetyl-β-

D-ribofuranosyl)thioacetoxy]mutilin (prepared as described in Example 41) according to the procedure of Example 18.

EXAMPLE 46

14-Deoxy-14-[(α-D-ribofuranosyl)thioacetoxy]-19,20-dihydromutilin, prepared from 14-deoxy-14-[(α-D-ribofuranosyl)thioacetoxy]mutilin (prepared as described in Example 44) according to the procedure of Example 19.

EXAMPLE 47

14-Deoxy-14-[(β-D-ribofuranosyl)thioacetoxy]-19,20-dihydromutilin, prepared from 14-deoxy-14-[(β-D-ribofuranosyl)thioacetoxy]mutilin (prepared as described in Example 45) according to the procedure of Example 19.

EXAMPLE 48

Preparation of 14-Deoxy-14-[(2-deoxy-2-(N,N-dimethylamino)-3,4,6-tri-O-acetyl-β-D-glucopyranosyl)thioacetoxy]mutilin To a solution of D-glucosamine hydrochloride (10.8 g, 0.05 mole) in water (250 ml) was added 250 ml of a 37% aqueous formaldehyde solution and 5 g of 10% palladium on carbon. The resulting mixture was hydrogenated until the theoretical uptake for conversion to 2-deoxy-2-(N,N-dimethylamino)-D-glucosamine was reached. The catalyst was removed by filtration, and the filtrate was lyophilized. The product obtained was acetylated with acetic anhydride and pyridine to give the corresponding tetra-O-acetyl derivative. This was converted to 2-deoxy-2-(N,N-dimethylamino)-3,4,6-tri-O-acetyl-D-glucopyranosyl bromide which was then converted to the corresponding 1-mercapto derivative according to the procedure described in Example 16. Coupling of 2-deoxy-2-(N,N-dimethylamino)-3,4,6-tri-O-acetyl-1-thio-D-glucopyranose with iodopleuromutilin according to the procedure of Example 16 Section C gave the desired product.

EXAMPLE 49

14-Deoxy-14-[(2-deoxy-2-(N,N-dimethylamino)-3,4,6-tri-O-acetyl-β-D-glucopyranosyl)thioacetoxy]-19,20-dihydromutilin, prepared from 14-deoxy-14-[(2-deoxy-2-(N,N-dimethylamino)-3,4,6-tri-O-acetyl-β-D-glucopyranosyl)thioacetoxy]mutilin (prepared as described in Example 48) according to the method of Example 17.

EXAMPLE 50

14-Deoxy-14-[(2-deoxy-2-(N,N-dimethylamino)-β-D-glucopyranosyl)thioacetoxy]mutilin, prepared from 14-deoxy-14-[(2-deoxy-2-(N,N-dimethylamino)-3,4,6-tri-O-acetyl-β-D-glucopyranosyl)thioacetoxy]mutilin (prepared as described in Example 48) according to the method of Example 18.

EXAMPLE 51

14-Deoxy-14-[(2-deoxy-2-(N,N-dimethylamino)-β-D-glucopyranosyl)thioacetoxy]-19,20-dihydromutilin, prepared from 14-deoxy-14-[(2-deoxy-2-(N,N-dimethylamino)-β-D-glucopyranosyl)thioacetoxy]mutilin (prepared as described in Example 50) according to the method of Example 19.

EXAMPLE 52

Preparation of 14-Deoxy-14-[(4-O-(2,3,4,6-tetra-O-acetyl-α-D-glucopyranosyl)-2,3,6-tri-O-acetyl-β-D-glucopyranosyl)thioacetoxy]mutilin This compound, hereinafter called the heptaacetyl thiomaltose derivative, was prepared according to the procedure described in Example 16, except that maltose octa-O-acetate was used as the starting material. Maltose octa-O-acetate was prepared as described in Methods, vol. 1, page 334; from this, hepta-O-acetyl maltose bromide was prepared according to the procedure described by Finan and Warren, J. Chem. Soc. 1962, 2823. Iodopleuromutilin (8.6 g) was reacted with hepta-O-acetyl maltose thiol (11.8 g; prepared by a procedure analogous to that described in Example 16 Sections A and B) according to the procedure of Example 16 Section C to give 17 g of product as a white foam. This product was submitted to further purification by HPLC, using an 8-liter gradient solvent from ethyl acetate to ethyl acetate:ethanol (1:1) to give 1.12 g of heptaacetyl thiomaltose derivative.

EXAMPLE 53

14-Deoxy-14-[4-O-(2,3,4,6-tetra-O-acetyl-α-D-glucopyranosyl)-2,3,6-tri-O-acetyl-β-D-glucopyranosyl)thioacetoxy]-19,20-dihydromutilin, hereinafter called dihydroheptaacetyl thiomaltose derivative, was prepared by reduction of the heptaacetyl thiomaltose derivative (330 mg) according to the procedure of Example 17 to give 334.5 mg of dihydroheptaacetyl thiomaltose derivative.

EXAMPLE 54

14-Deoxy-14-[(4-O-(α-D-glucopyranosyl)-β-D-glucopyranosyl)thioacetoxy]mutilin, hereinafter called the thiomaltose derivative, was prepared by deacetylation of the heptaacetyl thiomaltose derivative (1.1 g) according to the procedure described in Example 18 to give 1.1 g of crude product as a pale yellow residue. This product was further purified by HPLC, as described in Example 22, to give 732.6 mg of thiomaltose derivative.

EXAMPLE 55

14-Deoxy-14-[(4-O-(α-D-glucopyranosyl)-D-glucopyranosyl)thioacetoxy]-19,20-dihydromutilin, hereinafter called dihydrothiomaltose derivative, was prepared from the thiomaltose derivative (266.7 mg) by reduction according to the procedure described in Example 19 to give 243 mg of dihydrothiomaltose derivative.

EXAMPLES 56–83

The following compounds, prepared by the methods described in Examples 1–55:
14-deoxy-14-[(β-D-galactopyranosyl)oxyacetoxy]mutilin
14-deoxy-14-[(α-D-mannofuranosyl)oxyacetoxy]mutilin
14-deoxy-14-[(α-L-gulopyranosyl)oxyacetoxy]-19,20-dihydromutilin
14-deoxy-14-[(β-D-idopyranosyl)oxyacetoxy]mutilin
14-deoxy-14-[(α-D-altropyranosyl)oxyacetoxy]mutilin
14-deoxy-14-[(α-L-rhamnopyranosyl)oxyacetoxy]-19,20-dihydromutilin 14-deoxy-14-[(α-D-fucopyranosyl)thioacetoxy]mutilin 14-deoxy-14-[(α-D-galactofuranosyl)oxyacetoxy]mutilin 14-deoxy-14-[(α-D-mannopyranosyl)thioacetoxy]-19,20-dihydromutilin 14-deoxy-14-[(β-D-gulopyranosyl)thioacetoxy]mutilin 14-deoxy-14-[(β-D-idopyranosyl)thioacetoxy]-19,20-dihydromutilin 14-deoxy-14-[(α-D-rhamnopyranosyl)thioacetoxy]mutilin 14-deoxy-14-[(α-D-lyxopyranosyl)thioacetoxy]-19,20-dihydromutilin 14-deoxy-14-[(β-D-xylopyranosyl)thioacetoxy]mutilin 14-deoxy-14-[(2-deoxy-2-amino-α-D-mannopyranosyl)thioacetoxy]mutilin 14-deoxy-14-[(2-deoxy-2-(N-ethylamino)-α-D-glucopyranosyl)oxyacetoxy]mutilin 14-deoxy-14-[(2-deoxy-2-(N-tert-butylamino)-62 -D-xylopyranosyl)thioacetoxy]-19,20-dihydromutilin 14-deoxy-14-[(2-deoxy-2-(N-methylamino)-β-D-idopyranosyl)oxyacetoxy]mutilin 14-deoxy-14-[(2-deoxy-2-(N-methyl, N-ethylamino)-β-D-xylopyranosyl)thioacetoxy]-19,20-mutilin 14-deoxy-14-[(4-O-(β-D-galactopyranosyl)-β-D-glucopyranosyl)thioacetoxy]-19,20-dihydromutilin 14-deoxy-14-[(2,3,4-tri-O-butyryl-β-D-xylopyranosyl)thioacetoxy]mutilin 14-deoxy-14-[(2,3,4,6-tetra-O-propionyl-β-D-glucopyranosyl)oxyacetoxy]-19,20-dihydromutilin 14-deoxy-14-[(2-deoxy-2-(N,N-dimethylamino)-β-D-glucopyranosyl)thioacetoxy]mutilin 14-deoxy-14-[(2-deoxy-2-(N,N-dimethylamino)-β-D-glucopyranosyl)thioacetoxy]-19,20-dihydromutilin 14-deoxy-14-[(2-deoxy-2-(N,N-dimethylamino)-β-D-mannopyranosyl)thioacetoxy]mutilin 14-deoxy-14-[(2-deoxy-2-(N,N-dimethylamino)-β-D-mannopyranosyl)thioacetoxy]-19,20-dihydromutilin 14-deoxy-14-[(2-deoxy-2-(N,N-dimethylamino)-β-D-xylopyranosyl)thioacetoxy]mutilin 14-deoxy-14-[(2-deoxy-2-(N,N-dimethylamino)-β-D-xylopyranosyl)thioacetoxy]-19,20-dihydromutilin.

Activity of the Pleuromutilin Glycoside Derivatives

The compounds of this invention inhibit the growth of certain pathogenic organisms, particularly gram-positive bacteria. The compounds are conveniently tested against a typical gram-positive organism, Staphylococcus aureus, using a turbidometric assay on a semi-automated system (Autoturb Microbiological Assay System, Elanco) described by N. R. Kuzel and F. W. Kavanagh in J. Pharmaceut. Sci, 60 (5), 764 and 767 (1971). In testing these compounds, the following parameters were used: Staphylococcus aureus (H-Heatley) NRRL B-314 in a nutrient broth medium (pH 7), incubated for approximately 4 hours at 37° C. Test samples and A-40104 factor A, which is used as a standard, were dissolved in water. The standard was presented to the Autoturb carrousel at concentrations of 1.25, 2.50, 3.75, 5.00 and 6.25 mcg/ml. Test compounds were diluted to contain approximately 2.5 to 5.0 mcg of activity per ml, as presented to the carrousel. The units of activity of some of the typical compounds of this invention ($R^2$=H in group tested) in this in vitro assay are summarized in Table I

TABLE I

| Test Compound R | $R^1$ | Units of Activity (mcg/mg) |
|---|---|---|
| vinyl | β-D-xylopyranosyl (standard) | 446–452 |
| ethyl | α-D-glucopyranosyl | <100 |
| vinyl | 2,3,4-tri-O-acetyl-1-thio-β-D-xylopyranosyl | 568–579 |
| vinyl | 1-thio-β-D-xylopyranosyl | 995–1003 |
| ethyl | 1-thio-β-D-xylopyranosyl | 1150–1243 |
| ethyl | 2,3,4,6-tetra-O-acetyl-1-thio-β-D-glucopyranosyl | 203–220 |
| ethyl | 2,3,4-O-triacetyl-1-thio-β-D-xylopyranosyl | 746–883 |
| ethyl | 1-thio-β-D-glucopyranosyl | 29–31 |
| vinyl | β-D-glucopyranosyl | 12–13 |
| vinyl | 3,4,6-tri-O-acetyl-2-deoxy-2-(hydroxyimino)-α-D-glucopyranosyl | 11–12 |
| vinyl | 2,3,4,6-tetra-O-acetyl-β-D-glucopyranosyl | 75–85 |
| vinyl | 3,4,6-tri-O-acetyl-2-deoxy-2-(hydroxyimino)-α-D-galacttopyranosyl | 53–54 |
| vinyl | 1-thio-β-D-glucopyranosyl | 36 |
| vinyl | 2,3,4,6-tetra-O-acetyl-1-thio-β-D-glucopyranosyl | 253–265 |
| vinyl | 2,3,4-tri-O-acetyl-1-thio-α-D-ribopyranosyl | 50 |
| vinyl | 2,3,4-tri-O-acetyl-1-thio-β-D-ribopyranosyl | 325–360 |
| ethyl | 2,3,4-tri-O-acetyl-1-thio-β-D-ribopyranosyl | 480–500 |
| vinyl | 1-thio-β-D-ribopyranosyl | 1070 |
| ethyl | 1-thio-β-D-ribopyranosyl | 1500 |
| vinyl | 2,3,4-tri-O-acetyl-1-thio-β-D-ribopyranosyl | 30 |
| vinyl | 1-thio-α-D-ribopyranosyl | 350 |
| ethyl | 1-thio-α-D-ribopyranosyl | 430–433 |
| vinyl | 2,3,5-tri-O-acetyl-1-thio-α-D-ribopyranosyl | about 200 |
| vinyl | 2,3,5-tri-O-acetyl-1-thio-β-D-ribopyranosyl | about 450 |
| vinyl | hepta-O-acetyl-1-thiomaltose | 40 |
| ethyl | hepta-O-acetyl-1-thiomaltose | 28 |
| vinyl | 2,3,4-tri-O-acetyl-1-thio-β-D-arabinopyranosyl | 430 |
| ethyl | 2,3,4-tri-O-acetyl-1-thio-β-D-arabinopyranosyl | 380 |
| vinyl | 1-thio-β-D-arabinopyranosyl | 380 |
| ethyl | 1-thio-β-D-arabinopyranosyl | · 420 |
| ethyl | 4-deoxy-4-(dimethylamino)-β-D-xylopyranosyl | 300 |

The pleuromutilin glycosides of this invention are relatively nontoxic. For example, the $LD_{50}$'s of 14-deoxy-14-[(β-D-xylopyranosyl)thioacetoxy]mutilin and 14-deoxy-14-[(β-D-xylopyranosyl)thioacetoxy]-19,20-dihydromutilin, on intraperitoneal injection in mice, are greater than 1500 mg/kg; and the $LD_{50}$ of 14-deoxy-14-[(3,4,6-tri-O-acetyl-2-deoxy-2-(hydroxyimino)-α-D-glucopyranosyl)oxyacetoxy]-19,20-dihydromutilin, also on intraperitoneal injection in mice, is greater than 300 mg/kg.

Typical compounds of the present invention have shown in vivo antimicrobial activity against experimental bacterial infections. When two doses of these compounds were administered to mice in illustrative infections, the activity observed was measured as an $ED_{50}$ value [effective dose in mg/kg to protect 50% of the test animals; see Warren Wick, et al., J. Bacteriol. 81, 233–235 (1961)]. The $ED_{50}$ values observed for these compounds are given in Tables II and III.

TABLE II

| In Vivo Activity of 14-Deoxy-14-[(β-D-xylopyranosyl)thioacetoxy]mutilin | | | |
|---|---|---|---|
| Test Organism | Route | $ED_{50} \times 2$ | Infecting Challenge |
| Staphylococcus aureus 3055 | sc | 1.85 | 82 × $LD_{50}$ (ip) |
| Staphylococcus aureus 3055 | oral | 44 | 3400 × $LD_{50}$ (ip) |
| Staphylococcus aureus 3055 | oral | 32.4 | 500 × $LD_{50}$ (ip) |
| Streptococcus pyrogenes C203 | sc | 11.4 | 370 × $LD_{50}$ (ip) |

TABLE II-continued
In Vivo Activity of 14-Deoxy-14-[(β-D-xylopyranosyl)thioacetoxy]mutilin

| Test Organism | Route | ED$_{50}$ × 2 | Infecting Challenge |
|---|---|---|---|
| Streptococcus pneumoniae Park I | sc | 65 | 42 × LD$_{50}$ (ip) |
| Streptococcus pneumoniae B1492 | sc | 15.3 | 340 × LD$_{50}$ (ip) |

TABLE III
In Vivo Activity of 14-Deoxy-14-[(β-D-xylopyranosyl)-thioacetoxy]-19,20-dihydromutilin

| Test Organism | Route | ED$_{50}$ × 2 | Infecting Challenge |
|---|---|---|---|
| Staphylococcus aureus 3055 | sc | 1.6 | 400 × LD$_{50}$ (ip) |
| Staphylococcus aureus 3055 | oral | 29 | 3400 × LD$_{50}$ (ip) |
| Staphylococcus aureus 3055 | oral | 21 | 500 × LD$_{50}$ (ip) |
| Streptococcus pyrogenes C203 | sc | 7.0 | 500 × LD$_{50}$ (ip) |
| Streptococcus pneumoniae Park I | sc | 58.5 | 42 × LD$_{50}$ (ip) |
| Streptococcus pneumoniae B1343 | sc | 16.3 | 30 × LD$_{50}$ (ip) |
| Streptococcus pneumoniae B1492 | sc | 13.25 | 340 × LD$_{50}$ (ip) |

The compounds of this invention also inhibit the growth of a variety of anaerobic bacteria. Table IV summarizes the activity of typical compounds of this invention, as determined by the standard agar-dilution test.

cially needed for the prevention and treatment of mycoplasmal diseases of poultry, swine and cattle.

For example, 14-deoxy-14-[(β-D-xylopyranosyl)thioacetoxy]mutilin and 14-deoxy-14-[(β-D-xylopyranosyl)thioacetoxy]-19,20-dihydromutilin are

TABLE IV
MIC (mcg/ml)*
Compound Numbers

| | 1 | 2 | 3 | 4 | 5 | 6 | 7 | 8 | 9 | 10 | 11 |
|---|---|---|---|---|---|---|---|---|---|---|---|
| Actinomyces israelii | ≦0.5 | ≦0.5 | 0.5 | ≦0.5 | ≦0.5 | 2.0 | 64.0 | 8.0 | 1.0 | 2.0 | ≦0.5 |
| Clostridium perfringens | 16.0 | 2.0 | 2.0 | >128 | 8.0 | >128 | >128 | >128 | >128 | 64.0 | >128 |
| Clostridium septicum | ≦0.5 | 2.0 | 1.0 | 4.0 | 32.0 | 1.0 | >128 | >128 | >128 | 64.0 | 16.0 |
| Eubacterium aerofaciens | 16.0 | 1.0 | 0.5 | >128 | 4.0 | 16.0 | >128 | >128 | >128 | 16.0 | >128 |
| Peptococcus asaccharolyticus | ≦0.5 | ≦0.5 | 0.5 | ≦0.5 | 4.0 | 4.0 | 64.0 | 8.0 | 16.0 | 16.0 | ≦0.5 |
| Peptococcus prevoti | ≦0.5 | ≦0.5 | ≦0.125 | 8.0 | 2.0 | 2.0 | 128 | >128 | 16.0 | 16.0 | ≦0.5 |
| Peptostreptococcus anaerobius | ≦0.5 | ≦0.5 | ≦0.125 | 1.0 | 8.0 | ≦0.5 | 64.0 | 64.0 | 2.0 | ≦0.5 | ≦0.5 |
| Peptostreptococcus intermedius | ≦0.5 | ≦0.5 | 0.5 | 2.0 | 2.0 | 4.0 | >128 | >128 | >128 | 4.0 | 1.0 |
| Bacteroides fragilis 111 | 8.0 | 1.0 | 2.0 | 32.0 | 64.0 | 2.0 | >128 | >128 | >128 | 128 | 128 |
| Bacteroides fragilis 1877 | 4.0 | 1.0 | 1.0 | 32.0 | 64.0 | 2.0 | >128 | >128 | >128 | 64.0 | 32.0 |
| Bacteroides fragilis 1936B | 8.0 | 1.0 | 1.0 | 64.0 | 128 | 8.0 | >128 | >128 | >128 | 64.0 | 32.0 |
| Bacteroides thetaiotaomicron | 8.0 | 1.0 | 0.5 | 64.0 | 64.0 | 8.0 | >128 | >128 | >128 | 64.0 | 16.0 |
| Bacteroides melaninogenicus 1856/28 | >128 | >128 | 0.25 | 8.0 | 2.0 | 2.0 | >128 | >128 | >128 | >128 | >128 |
| Bacteroides melaninogenicus 2736 | 2.0 | 1.0 | 0.5 | 4.0 | 4.0 | 4.0 | 32 | >128 | >128 | 32.0 | 16.0 |
| Bacteroides vulgatis | 4.0 | 1.0 | 1.0 | 32.0 | 32.0 | 4.0 | >128 | >128 | >128 | 64.0 | 32.0 |
| Bacteroides corrodens | 4.0 | 1.0 | 1.0 | 32.0 | 64.0 | 4.0 | >128 | >128 | >128 | 64.0 | 32.0 |
| Fusobacterium symbiosum | 4.0 | 2.0 | 1.0 | 128 | 16.0 | 4.0 | >128 | >128 | >128 | 64.0 | 128 |
| Fusobacterium necrophorum | ≦0.5 | ≦0.5 | 1.0 | ≦0.5 | 8.0 | 4.0 | >128 | >128 | 64.0 | 2.0 | 16.0 |

*Endpoint read after 24-hour incubation

Compound
| No. | Name |
|---|---|
| 1 | 14-deoxy-14-[(2,3,4-tri-O-acetyl-β-D-xylopyranosyl)thioacetoxy]mutilin |
| 2 | 14-deoxy-14-[(β-D-xylopyranosyl)thioacetoxy]mutilin |
| 3 | 14-deoxy-14-[(β-D-xylopyranosyl)thioacetoxy]-19,20-dihydromutilin |
| 4 | 14-deoxy-14[(2,3,4,6-tetra-O-acetyl-β-D-glucopyranosyl)thioacetoxy]-19,20-dihydromutilin |
| 5 | 14-deoxy-14-[(β-D-glucopyranosyl)thioacetoxy]-19,20-dihydromutilin |
| 6 | 14-deoxy-14-[(2,3,4-tri-O-acetyl-β-D-xylopyranosyl)thioacetoxy]-19,20-dihydromutilin |
| 7 | 14-deoxy-14-[(3,4,6-tri-O-acetyl-2-deoxy-2-(hydroxyimino)-α-D-glucopyranosyl)oxyacetoxy]mutilin |
| 8 | 14-deoxy-14-[(3,4,6-tri-O-acetyl-2-deoxy-2-(hydroxyimino)-α-D-glucopyranosyl)oxyacetoxy]-19,20-dihydromutilin |
| 9 | 14-deoxy-14-[(3,4,6-tri-O-acetyl-2-deoxy-2-(hydroxyimino)-α-D-galactopyranosyl)oxyacetoxy]mutilin |
| 10 | 14-deoxy-14-[(β-D-glucopyranosyl)thioacetoxy]mutilin |
| 11 | 14-deoxy-14-[(2,3,4,6-tetra-O-acetyl-β-D-glucopyranosyl)thioacetoxy]-multilin |

An important aspect of the activity of the compounds of this invention is their activity against mycoplasmas. Mycoplasma species are pathogenic to man and various animals. Agents active against mycoplasmas are especially active in in vitro tests against isolates of *Ureaplasma sp., Mycoplasma bovis, Mycoplasma dispar,* and several other species of bovine mycoplasmas at levels as low as 0.024 mcg/ml.

The minimal inhibitory concentrations (MIC's) of a number of typical compounds of the present invention ($R^2$=H in group tested) against various mycoplasma species, as determined by in vitro broth-dilution studies, are summarized in Table V.

TABLE V

| Test Compound | | MIC (mcg/ml) | | | |
|---|---|---|---|---|---|
| R | $R^1$ | Mycoplasma gallisepticum | Mycoplasma synoviae | Mycoplasma hyorhinis | Mycoplasma hyopneumoniae |
| ethyl | 3,4,6-tri-O-acetyl-2-deoxy-2-(hydroxyimino)-α-D-glucopyranosyl | 3.12 | 6.25 | 6.25 | |
| vinyl | β-D-glucopyranosyl | 0.39 | 0.78 | 0.78 | |
| vinyl | 2,3,5,6-tetra-O-acetyl-β-D-glucopyraosyl | 0.78 | 0.78 | 0.78 | |
| vinyl | 3,4,6-tri-O-acetyl-2-deoxy-2-(hydroxyimino)-α-D-glucopyranosyl | 0.78 | >6.25 | 0.78 | |
| vinyl | 1-thio-β-D-xylopyranosyl | 0.78 | 0.78 | 0.39 | ≦0.15 |
| ethyl | 1-thio-β-D-xylopyranosyl | 0.39 | 0.39 | 0.39 | ≦0.15 |
| ethyl | 2,3,4-tri-O-acetyl-1-thio-β-D-xylopyranosyl | 0.78 | 0.78 | 0.39 | ≦0.15 |
| vinyl | 3,4,6-tri-O-acetyl-2-deoxy-2-(hydroxyimino)-α-D-galactopyranosyl | <0.78 | <0.78 | 1.56 | 0.78 |
| vinyl | 2,3,4,6-tetra-O-acetyl-1-thio-β-D-glucopyranosyl | >0.78 | 1.56 | >0.78 | |
| vinyl | 1-thio-β-D-glucopyranosyl | 1.56 | 3.12 | 1.56 | |
| vinyl | 2,3,4,6-tetra-O-benzyl-α-D-glucopyranosyl | 25.0 | 50.0 | 50.0 | |

The compounds of this invention also exhibit in vitro activity against *Pasteurella multocida*, *Pasteurella hemolytica*, and a Pseudomonas species which is pathogenic to fish. *P. multocida*, for example, is a causative agent of respiratory infection in cattle, poultry and swine. *P. hemolytica* is a major cause of respiratory disease in cattle.

In in vitro tests against *Pasteurella hemolytica*, for example, the mean MIC values for 14-deoxy-14-[(β-D-xylopyranosyl)thioacetoxy]mutilin and 14-deoxy-14-[(β-D-xylopyranosyl)thioacetoxy]-19,20-dihydromutilin were 12.5 mcg/ml and 10.4 mcg/ml, respectively.

The activity of representative compounds of this invention ($R^2$=H in group tested) against *P. multocida* and the *Pseudomonas sp.* is summarized in Table VI.

TABLE VI

| | Test Compound | MIC (mcg/ml) | | |
|---|---|---|---|---|
| R | $R^1$ | Pasteurella multocida (bovine) | Pasteurella multocida (turkey) | Pseudomonas sp. (fish) |
| vinyl | 1-thio-β-D-xylopyranosyl | 3.12 | 6.25 | 6.25 |
| ethyl | 1-thio-β-D-xylopyranosyl | 6.25 | 6.25 | 12.5 |
| ethyl | 2,3,4-tri-O-acetyl-1-thio-β-D-xylopyranosyl | <50.0 | <50.0 | 12.5 |
| vinyl | 2,3,4-tri-O-acetyl-1-thio-β-D-xylopyranosyl | <50.0 | 50.0 | 12.5 |

TABLE VII

| Test Compound | | Activity - ppm | | | |
|---|---|---|---|---|---|
| R | $R^1$ | 1.0 | 0.1 | 0.05 | 0.01 |
| ethyl | 1-thio-β-D-xylopyranosyl | R | R | R | R |
| vinyl | 2,3,4-tri-O-acetyl-1-thio-β-D-xylopyranosyl | R,R | R,R | —,R | Y,RO |
| ethyl | 2,3,4-tri-O-acetyl-1-thio-β-D-xylopyranosyl | R | R | R | RO |
| vinyl | 1-thio-β-D-xylopyranosyl | R,R | R,R | —,R | RO,RO |
| ethyl | 2,3,4,6-tetra-O-acetyl-1-thio-β-D-glucopyranosyl | R | R | R | Y |
| ethyl | 1-thio-β-D-glucopyranosyl | R | R | R | Y |
| vinyl | 2,3,4,6-tetra-O-acetyl-β-D-glucopyranosyl | R | YO | — | — |
| vinyl | β-D-glucopyranosyl | R | Y | — | — |
| ethyl | 3,4,6-tri-O-acetyl-2-deoxy-2-(hydroxyimino)-α-D-glucopyranosyl | R | Y | — | — |

An important aspect of this invention is the use of the compounds of this invention in the treatment of swine dysentery. As discussed by W. E. Brown et al. in U.S. Pat. No. 4,041,175, pleuromutilin is effective in the treatment of swine dysentery. I have discovered that the pleuromutilin glycoside derivatives of this invention are also active against *Treponema hyodysenteriae*, the organism most commonly associated with swine dysentery. The activity against *T. hyodysenteriae* was determined using an in vitro test. The test involved incorporating the compound at levels of 50, 5.0, 0.5 and 0.05 mcg/ml in trypticase soy agar plates containing 5% bovine defibrinated blood. The agar surface was inoculated with 0.1 ml of a $10^{-1}$ dilution of a suspension of *T. hyodysenteriae*. Plates were incubated under anaerobic conditions for four days and then evaluated for presence or absence of growth of hemolytic treponema. 14-Deoxy-14-[(β-D-xylopyranosyl)thioacetoxy]mutilin and 14-deoxy-14-[(β-D-xylopyranosyl)thioacetoxy]-19,20-dihydromutilin inhibited growth at the 50, 5.0 and 0.5 mcg/ml agar concentrations.

In another important aspect, the compounds of this invention are active against Spiroplasmas. *Spiroplasma citri* is the causative agent of citrus-stubborn disease; another Spiroplasma, corn-stunt Spiroplasma, affects the growth of corn. Table VII summarizes the in vitro activity of representative compounds of the present invention ($R^2$=H in this group) against *Spiroplasma citri*. In this test, inhibition of *S. citri* is measured by a color reaction. Red (R) includes complete inhibition; red-orange (RO) indicates partial inhibition; and yellow (Y) indicates no inhibition. Thus, for example, 14-deoxy-14-[(β-D-xylopyranosyl)thioacetoxy]-19,20-dihydromutilin inhibits the growth of *S. citri* at levels as low as 0.01 ppm.

When used for the treatment of swine dysentery, the compounds of this invention can be administered orally to swine infected with the disease in the form of a tablet, capsule, powder or the like. A preferred method of administration, however, is to incorporate the compound in the swine feed ration.

I claim:

1. A compound of the formula:

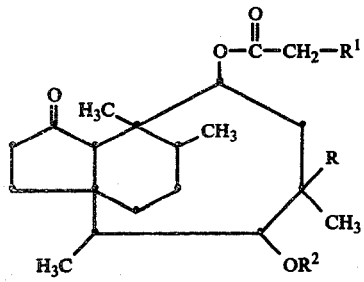

wherein R is ethyl or vinyl; $R^1$ is selected from the group consisting of:

(a) the α- and β-anomers of the following hexopyranoses and hexofuranoses: D- and L-glucose; D- and L-galactose; D- and L-mannose; D- and L-gulose; D- and L-idose; D- and L-altrose; L- and D-rhamnose; D- and L-fucose; 1-thio-D- and L-glucose; 1-thio-D- and L-galactose; 1-thio-D- and L-mannose; 1-thio-D- and L-gulose; 1-thio-D- and L-idose; 1-thio-D- and L-altrose; 1-thio-L- and D-rhamnose; and 1-thio-D- and L-fucose;

(b) the α- and β-anomers of the following pentopyranoses and pentofuranoses: D- and L-lyxose, D- and L-ribose, L- and D-arabinose, D- and L-2-deoxyribose; 1-thio-D- and L-lyxose, 1-thio-D- and L-ribose, 1-thio-L- and D-arabinose; and D- and L-2-deoxy-1-thioribose;

(c) the α- and β-anomers of the following pentofuranoses: D- and L-xylose and 1-thio-D- and L-xylose;

(d) the α- and β-anomers of the pentopyranose forms of L-xylose and 1-thio-D- and L-xylose;

(e) the α-anomer of the pentopyranoses form of D-xylose;

(f) the α- and β-anomers of the following pyranose and furanose aminosugars: 2-deoxy-2-amino-D- and L-glucose; 2-deoxy-2-amino-D- and L-mannose; 2-deoxy-2-amino-D- and L-xylose; 2-deoxy-2-amino-D- and L-lyxose, 2-deoxy-2-amino-D- and L-galactose; 4-deoxy-4-amino-D- and L-xylose; 2-deoxy-2-amino-1-thio-D- and L-glucose; 2-deoxy-2-amino-1-thio-D- and L-mannose; 2-deoxy-2-amino-1-thio-D- and L-xylose; 2-deoxy-2-amino-1-thio-D- and L-lyxose; 1-thio-D- and L-galactosamine; 4-deoxy-4-amino-1-thio-D- and L-xylose; and the N-mono($C_1$–$C_4$)alkyl and N,N-di($C_1$–$C_4$)alkyl derivatives of these aminosugars;

(g) the α- and β-anomers of the following disaccharides: maltose, cellobiose; lactose; gentiobiose; isomaltose; melibiose; raffinose; and xylobiose; 1-thiomaltose; 1-thiocellobiose; 1-thiolactose; 1-thiogentiobiose; 1-thioisomaltose; 1-thiomelibiose, 1-thioraffinose; and 1-thioxylobiose;

(h) the α- and β-anomers of the trisaccharides maltotriose; cellotriose; xylotriose; 1-thiomaltotriose; 1-thiocellotriose and 1-thioxylotriose;

(i) 2-deoxy-2-(hydroxyimino)-3,4,6-tri-O-acetyl-α-D-glucopyranoxyl; 2-deoxy-2-(hydroxyimino)-3,4,6-tri-O-acetyl-α-D-galactopyranosyl; 2-deoxy-2-(hydroxyimino)-α-D-galactopyranosyl; 2-deoxy-2-amino-4,6-di-O-acetyl-α-D-glucopyranosyl; 2-deoxy-2-acetamido-3,4,6-tri-O-acetyl-α-D-glucopyranosyl;

(j) and any of the (a) through (h) moieties peracylated with $C_2$–$C_4$-alkanoyl or benzoyl;

$R^2$ is hydrogen or, when $R^1$ is selected from the group defined in (j), $C_2$–$C_6$-alkanoyl or benzoyl; and the pharmaceutically acceptable acid-addition salts of the compounds wherein $R^1$ is selected from the group defined in (f).

2. 14-deoxy-14-[(2,3,4,6-tetra-O-benzyl-α-D-glucopyranosyl)oxyacetoxy]-mutilin.

3. The compound of claim 1 which is 14-deoxy-14-[(α-D-glucopyranosyl)oxyacetoxy]mutilin.

4. The compound of claim 1 which is 14-deoxy-14-[(2,3,4,6-tetra-O-acetyl-β-D-glucopyranosyl)oxyacetoxy]mutilin.

5. The compound of claim 1 which is 14-deoxy-14-[(β-D-glucopyranosyl)oxyacetoxy]mutilin.

6. The compound of claim 1 which is 14-deoxy-14-[(2-deoxy-2-amino-4,6-di-O-acetyl-α-D-glycopyranosyl)oxyacetoxy]-19,20-dihydromutilin.

7. The compound of claim 1 which is 11-acetyl-14-deoxy-14-[(2-deoxy-2-acetamido-3,4,6-tri-O-acetyl-α-D-glucopyranosyl)oxyacetoxy]-19,20-dihydromutilin.

8. The compound of claim 1 which is 14-deoxy-14-[(2-deoxy-2-amino-α-D-galactopyranosyl)oxyacetoxy]-19,20-dihydromutilin.

9. The compound of claim 1 which is 14-deoxy-14-[(2,3,4,6-tetra-O-acetyl-β-D-glucopyranosyl)thioacetoxy]mutilin.

10. The compound of claim 1 which is 14-deoxy-14-[(2,3,4,6-tetra-O-acetyl-β-D-glucopyranosyl)thioacetoxy]-19,20-dihydromutilin.

11. The compound of claim 1 which is 14-deoxy-14-[(β-D-glucopyranosyl)thioacetoxy]mutilin.

12. The compound of claim 1 which is 14-deoxy-14-[(β-D-glucopyranosyl)thioacetoxy]-19,20-dihydromutilin.

13. The compound of claim 1 which is 14-deoxy-14-[(2,3,4-tri-O-acetyl-β-D-xylopyranosyl)thioacetoxy]mutilin.

14. The compound of claim 1 which is 14-deoxy-14-[(2,3,4-tri-O-acetyl-β-D-xylopyranosyl)thioacetoxy]-19,20-dihydromutilin.

15. The compound of claim 1 which is 14-deoxy-14-[(β-D-xylopyranosyl)thioacetoxy]mutilin.

16. The compound of claim 1 which is 14-deoxy-14-[(β-D-xylopyranosyl)thicacetoxy]-19,20-dihydromutilin.

17. The compound of claim 1 which is 14-deoxy-14-[(2,3,4-tri-O-acetyl-β-D-arabinopyranosyl)thioacetoxy]mutilin.

18. The compound of claim 1 which is 14-deoxy-14-[(2,3,4-tri-O-acetyl-β-L-arabinopyranosyl)thioacetoxy]mutilin.

19. The compound of claim 1 which is 14-deoxy-14-[(β-D-arabinopyranosyl)thioacetoxy]mutilin.

20. The compound of claim 1 which is 14-deoxy-14-[(β-L-arabinopyranosyl)thioacetoxy]mutilin.

21. The compound of claim 1 which is 14-deoxy-14-[(2,3,4,6-tetra-O-acetyl-β-D-galactopyranosyl)thioacetoxy]mutilin.

22. The compound of claim 1 which is 14-deoxy-14-[(β-D-galactopyranosyl)thioacetoxy]mutilin.

23. The compound of claim 1 which is 14-deoxy-14-[(2,3,4-tri-O-acetyl-β-D-arabinopyranosyl)thioacetoxy]-19,20-dihydromutilin.

24. The compound of claim 1 which is 14-deoxy-14-[(2,3,4-tri-O-acetyl-β-L-arabinopyranosyl)thioacetoxy]-19,20-dihydromutilin.

25. The compound of claim 1 which is 14-deoxy-14-[(β-D-arabinopyranosyl)thioacetoxy]-19,20-dihydromutilin.

26. The compound of claim 1 which is 14-deoxy-14-[(β-L-arabinopyranosyl)thioacetoxy]-19,20-dihydromutilin.

27. The compound of claim 1 which is 14-deoxy-14-[(2,3,4,6-tetra-O-acetyl-β-D-galactopyranosyl)thioacetoxy]-19,20-dihydromutilin.

28. The compound of claim 1 which is 14-deoxy-14-[(β-D-galactopyranosyl)thioacetoxy]-19,20-dihydromutilin.

29. The compound of claim 1 which is 14-deoxy-14-[(4-deoxy-4-(dimethylamino)-β-D-xylopyranosyl)oxyacetoxy]-19,20-dihydromutilin.

30. The compound of claim 1 which is 14-deoxy-14-[(2,3,4-tri-O-acetyl-β-D-ribopyranosyl)thioacetoxy]-mutilin.

31. The compound of claim 1 which is 14-deoxy-14-[(β-D-ribopyranosyl)thioacetoxy]mutilin.

32. The compound of claim 1 which is 14-deoxy-14-[(α-D-ribopyranoysl)thioacetoxy]-19,20-dihydromutilin.

33. The compound of claim 1 which is 14-deoxy-14-[(β-D-ribopyranosyl)thioacetoxy]-19,20-dihydromutilin.

34. The compound of claim 1 which is 14-deoxy-14-[(2-deoxy-2-(N,N-dimethylamino)-β-D-glucopyranosyl)thioacetoxy]mutilin.

35. The compound of claim 1 which is 14-deoxy-14-[(2-deoxy-2-(N,N-dimethylamino)-β-D-glucopyranosyl)thioacetoxy]-19,20-dihydromutilin.

36. The compound of claim 1 which is 14-deoxy-14-[(2-deoxy-2-(N,N-dimethylamino)-β-D-mannopyranosyl)thioacetoxy]mutilin.

37. The compound of claim 1 which is 14-deoxy-14-[(2-deoxy-2-(N,N-dimethylamino)-β-D-mannopyranosyl)thioacetoxy]-19,20-dihydromutilin.

38. The compound of claim 1 which is 14-deoxy-14-[(2-deoxy-2-(N,N-dimethylamino)-β-D-xylopyranosyl)-thioacetoxy]mutilin.

39. The compound of claim 1 which is 14-deoxy-14-[(2-deoxy-2-(N,N-dimethylamino)-β-D-xylopyranosyl)-thioacetoxy]-19,20-dihydromutilin.

* * * * *

UNITED STATES PATENT AND TRADEMARK OFFICE
CERTIFICATE OF CORRECTION

PATENT NO. : 4,130,709

DATED : December 19, 1978

INVENTOR(S) : Ramakrishnan Nagarajan

It is certified that error appears in the above-identified patent and that said Letters Patent are hereby corrected as shown below:

Column 1, line 13, that part of the structural formula reading

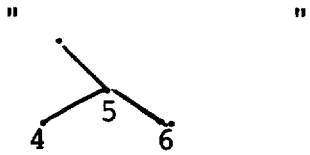

should read

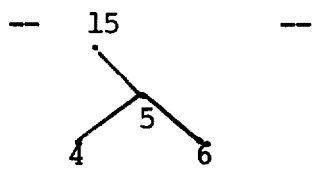

Column 1, lines 44 and 46, "Reidl" should read -- Riedl --.

Column 2, line 19, "62-configu-" should read -- $\beta$-configu- --.

UNITED STATES PATENT AND TRADEMARK OFFICE
CERTIFICATE OF CORRECTION

PATENT NO. : 4,130,709
DATED : December 19, 1978
INVENTOR(S) : Ramakrishnan Nagarajan It is certified that error appears in the above-identified patent and that said Letters Patent are hereby corrected as shown below:

Column 3, line 23, "2acetamido" should read -- 2-acetamido --.

Column 5, line 11, "acetate; toluene" should read -- acetate:toluene --; line 57, "satureated" should read -- saturated --.

Column 10, line 33, "thioronium" should read -- thiouronium --; line 39, "thioronium" should read -- thiouronium --; line 44, "THe" should read -- The --.

Column 12, line 55, "arabinopyranoxyl" should read -- arabinopyranosyl --.

Column 13, line 40, "arbinopyranosyl" should read -- arabinopyranosyl --.

Column 16, line 27, "toluene-ethyl" should read -- toluene:ethyl --.

Column 19, line 18, "62 -D-" should read -- β-D- --.

Column 20, line 3, there should be a period after "Table I"; line 20, "galacttopyranosyl" should read -- galactopyranosyl --.

Column 21, line 63, "multilin" should read -- mutilin --.
Column 25, line 70, "glucopyranoxyl" should read -- glucopyranosyl --.

UNITED STATES PATENT AND TRADEMARK OFFICE
CERTIFICATE OF CORRECTION

PATENT NO. : 4,130,709

DATED : December 19, 1978

INVENTOR(S) : Ramakrishnan Nagarajan

It is certified that error appears in the above-identified patent and that said Letters Patent are hereby corrected as shown below:

Column 23, line 13, "2,3,5,6-tetra" should read -- 2,3,4,6-tetra --; line 63, "includes" should read -- indicates --.

Column 28, line 4, "ribopyranoysl" should read -- ribopyranosyl --.

UNITED STATES PATENT AND TRADEMARK OFFICE
CERTIFICATE OF CORRECTION

PATENT NO. : 4,130,709

DATED : December 19, 1978

INVENTOR(S) : Ramakrishnan Nagarajan

It is certified that error appears in the above-identified patent and that said Letters Patent are hereby corrected as shown below:

Column 3, line 66, "thioglycosides" should read -- thioglycoside --.

Column 13, line 39, "14-[β-L-" should read -- 14-[(β-L- --; line 61, "14-Deoxy-14-[β-D-galactopyranosyl)" should read -- 14-Deoxy-14-[(2,3,4,6-tetra-O-acetyl-β-D-galactopyranosyl) --.

Column 15, line 15, "chloroform" should read -- carbon tetrachloride --.

Column 19, line 23, "19,20-mutilin" should read -- 19,20-dihydromutilin --.

Column 20, line 13, "O-triacetyl" should read -- tri-O-acetyl --.

Column 25, line 8, "formulaa" should read -- formula --.

Signed and Sealed this

Twenty-seventh Day of November 1979

[SEAL]

Attest:

RUTH C. MASON
*Attesting Officer*

LUTRELLE F. PARKER
*Acting Commissioner of Patents and Trademarks*